US00PP17214P2

(12) United States Plant Patent
Giesen

(10) Patent No.: US PP17,214 P2
(45) Date of Patent: Nov. 14, 2006

(54) ***SANVITALIA* PLANT NAMED 'SAN YEL'**

(50) Latin Name: *Sanvitalia procumbens*
Varietal Denomination: San Yel

(75) Inventor: Eric Giesen, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 2 days.

(21) Appl. No.: 11/216,190

(22) Filed: Aug. 31, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—Jondle & Associates P.C.

(57) ABSTRACT

A new *Sanvitalia* plant particularly distinguished by its compact, low mounding, and spreading habit, early flowering, large flowers, good vigor, and good branching habit is disclosed.

1 Drawing Sheet

Genus and species: *Sanvitalia procumbens*.
Variety denomination: 'San Yel'.

BACKGROUND OF THE NEW PLANT

The present invention comprises a new and distinct cultivar of *Sanvitalia*, botanically known as *Sanvitalia procumbens*, and hereinafter referred to by the cultivar name 'San Yel'. The new cultivar originated from a hybridization made in 2003 in Andijk, The Netherlands. The female parent is 'SAN03-18-1' an unpatented yellow *Sanvitalia* proprietary line, and the male parent is 'SAN02-2-1' an unpatented yellow *Sanvitalia* proprietary line.

The new cultivar was created in 2003 in Andijk, The Netherlands and has been asexually reproduced repeatedly by vegetative cuttings and tissue culture in Andijk, The Netherlands over a two-year period. The plant has also been trialed at Gilroy, Calif., Litchfield, Mich., and Andijk, The Netherlands. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif. and Andijk, The Netherlands.

1. Compact, low-mounding, and spreading habit;
2. Early flowering;
3. Large flowers;
4. Good vigor; and
5. Good branching habit.

DESCRIPTION OF PHOTOGRAPH

This new *Sanvitalia* plant is illustrated by the accompanying photograph which shows blooms, buds, and foliage of the plant in full color; the colors shown are as true as can be reasonably obtained by conventional photographic procedures. The photograph is of a four and one-half month-old plant grown in a greenhouse with natural light in a late winter/spring trial setting.

The accompanying photograph shows blooms, buds, mature foliage, and plant habit; the inset shows mature inflorescences.

DESCRIPTION OF THE NEW CULTIVAR

The following detailed descriptions set forth the distinctive characteristics of 'San Yel'. The data which define these characteristics were collected from asexual reproductions carried out in Gilroy, Calif. The plant history was taken on six-month-old plants grown in four-inch pots in a poly-covered greenhouse. Color readings were taken in the greenhouse in the summer season under natural light. Color references are primarily to The R.H.S. Colour Chart of The Royal Horticultural Society of London (R.H.S.) (2001 edition). Texture description details were observed under a dissecting microscope.

DESCRIPTION OF THE NEW PLANT

Classification:
*Botanical name.*—*Sanvitalia procumbens.*
Parentage:
*Female parent.*—'SAN03-18-1' proprietary *Sanvitalia* line (unpatented).
*Male parent.*—'SAN02-2-1' proprietary *Sanvitalia* line (unpatented).
Growth:
*Form and habit.*—Low mounding and compact with a spreading habit.
*Growth and branching habit.*—Vigorous, well-branched, and flowers early.
*Height (from top of soil).*—10–15 cm.
*Width (including flowers).*—20–30 cm.
*Time to produce a finished flowering plant.*—6–9 weeks for a 4-inch pot.
*Outdoor plant performance.*—Use as patio planters, in mixed container plantings, or in hanging baskets.
*Time to initiate and develop roots.*—14–16 days.
*Root description.*—Fibrous, freely branching, and white.
Leaves:
*Arrangement.*—Simple and opposite with no petioles.
*Shape.*—Lanceolate.

*Apex.*—Broadly acute.
*Base.*—Truncate.
*Margin.*—Entire.
*Immature.*—Length: 2.0–2.2 cm. Width: 0.9–1.1 cm.
*Mature* (*fully expanded*).—Length: 2.7–3.0 cm. Width: 1.0–1.3 cm.
*Color* (*immature and mature).*—Upper surface: Closest to RHS 139, but with more grey. Lower surface: Closest to RHS N138C.
*Venation.*—Type: Pinnate. Color: RHS 144B.
*Texture.*—Hirsute.

Stems:
*Length.*—15–23 cm.
*Diameter.*—0.2–0.25 cm.
*Internode length.*—2.5–4.0 cm.
*Color.*—RHS 146.
*Texture.*—Pubescent.
*Anthocyanin.*—Present.

Bud:
*Shape.*—Round.
*Diameter.*—0.4–0.6 cm.
*Length.*—0.2–0.3 cm.
*Color* (*at tight bud, when starting to show color*).—RHS 14A.

Inflorescence:
*Type.*—Composite-type, solitary inflorescences born terminally above the foliage.
*Blooming habit.*—Plants start to bloom early and are continuously flowering through the spring, summer, and fall.
*Quantity of inflorescences per plant.*—Greater than 50.
*Lastingness of individual blooms on the plant.*—2–3 weeks.
*Fragrance.*—None.
*Inflorescence diameter.*—Immature: 0.5–0.6 cm. Mature: 1.5–1.8 cm.
*Disc diameter.*—0.6–0.7 cm.
*Disc floret.*—Quantity (per inflorescence): 75–100. Shape: Tubular and elongated. Tube color: Immature: Closest to RHS 144D. Mature: RHS 10D. Length: 0.3 cm. Diameter (at apex): 0.075 cm. Apex: Acute, 5 pointed. Apex color: RHS 14B. Base: Fused.
*Ray floret.*—Quantity: 12–13. Shape: Broadly linear. Color, immature: Upper surface: RHS 14A. Lower surface: RHS 7A. Color, mature: Upper surface: Closest to RHS 14A. Lower surface: Closest to RHS 7A. Length: 0.5–0.6 cm. Width: 0.2 cm. Apex: Irregularly emarginate. Base: Fused. Margin: Entire. Texture: Papillose.
*Penduncle.*—Color: RHS 146C with a heavy hue of anthocyanin, giving a colored overlay hue of approximately RHS 174A. Length: 0.5–1.5 cm. Diameter: 0.1 cm. Texture: Heavily pubescent.
*Phyllaries.*—Quantity (per inflorescence): 5. Shape: Ovate. Color: Upper surface: RHS 137B. Lower surface: RHS 138A. Length: 0.5 cm. Width: 0.4 cm. Apex: Acute. Base: Fused. Margin: Entire. Texture: Pubescent and very heavily pubescent basally.

Reproductive organs:
*Androecium.*—Location: Present on disc florets only. Stamen quantity: 5 per floret. Filament: Color: RHS 155C, but lighter. Length: 0.2 cm. Anther: Anther color: RHS 14A. Pollen color: RHS 14B, but lighter. Pollen amount: Moderate to scarce.
*Gynoecium.*—Location: Present on ray and disc florets. Pistil length: 0.2–0.3 cm. Pistil quantity: 1 per floret. Stigma: Color: RHS 14A. Shape: Bi-parted. Style: Length: 0.2 cm. Color: RHS 14A.

Fruit and seed set: Has not been observed.
Disease and insect resistance: Has not been observed.

COMPARISON WITH PARENTAL AND COMMERCIAL CULTIVARS

'San Yel' differs from the female parent, 'SAN03-18-1' proprietary line (unpatented), in that 'San Yel' has a larger flower size and a larger plant size, by about 10 cm, than 'SAN03-18-1'.

'San Yel' differs from the male parent, 'SAN02-2-1' proprietary line (unpatented), in that 'San Yel' has shorter internodes, more vigor, and a more compact plant habit than 'SAN02-2-1'.

'San Yel' differs from the commercial cultivar 'Santis 999-3' (U.S. Plant Pat. No. 12,297) in that 'San Yel' has narrower leaves, larger flowers and sepals, and a more rounded plant habit than 'Cuzco Yellow'.

I claim:

1. A new and distinct cultivar of *Sanvitalia* plant as shown and described herein.

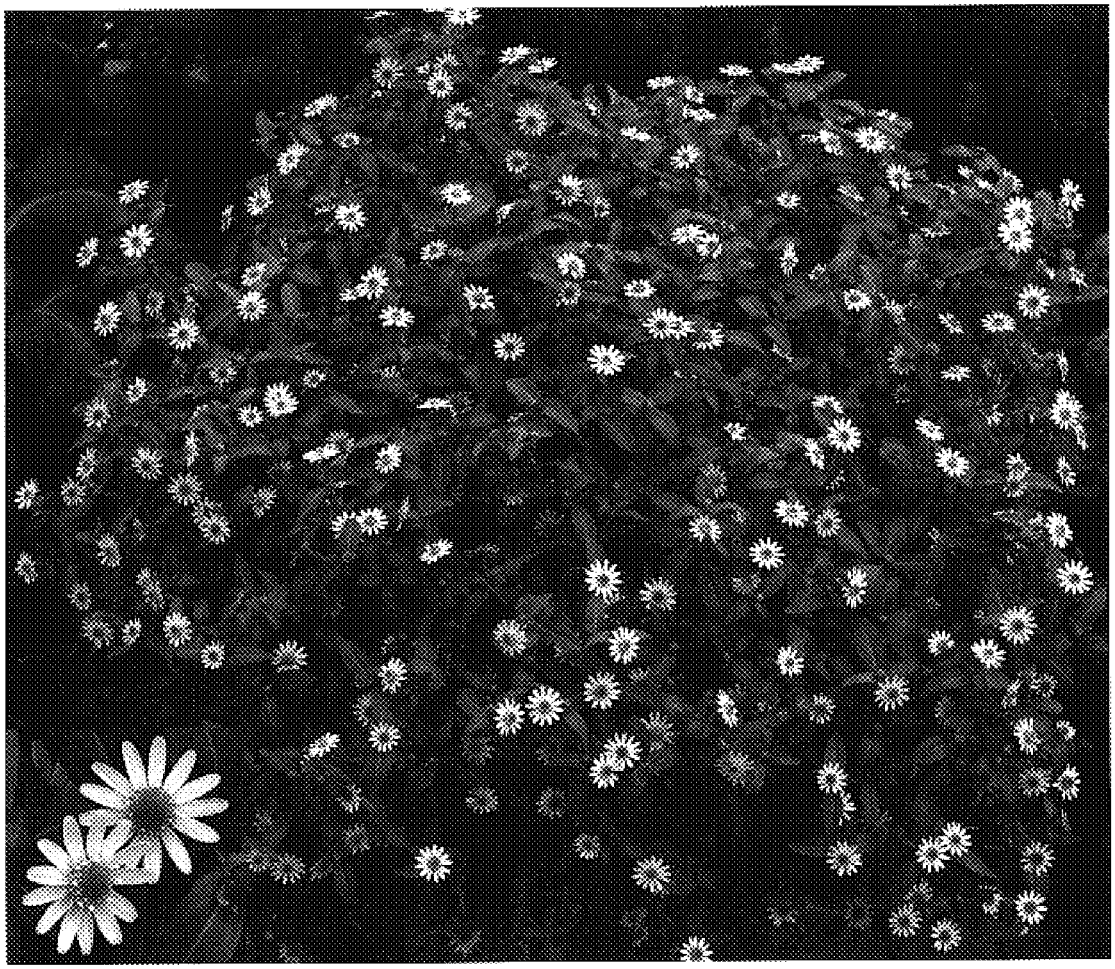

* * * * *